(12) United States Patent
Maus et al.

(10) Patent No.: US 8,008,319 B2
(45) Date of Patent: Aug. 30, 2011

(54) TREATMENT OF COLORECTAL POLYPS WITH IMIDAZOQUINOLINE DERIVATIVES

(75) Inventors: Joachim Maus, Mülheim (DE); Istvan Szelenyi, Schwaig (DE); Ursula Petzold, Friedrichsdorf-Koeppem (DE)

(73) Assignee: Meda Pharma GmbH & Co. KG, Homburg (DE)

( * ) Notice: Subject to any disclaimer, the term of this patent is extended or adjusted under 35 U.S.C. 154(b) by 53 days.

(21) Appl. No.: 12/353,683

(22) Filed: Jan. 14, 2009

(65) Prior Publication Data

US 2009/0182005 A1    Jul. 16, 2009

Related U.S. Application Data

(60) Provisional application No. 61/006,459, filed on Jan. 15, 2008.

(51) Int. Cl.
*A61K 31/4745* (2006.01)
*A61K 31/4375* (2006.01)

(52) U.S. Cl. .................................................. 514/293

(58) Field of Classification Search .................. None
See application file for complete search history.

(56) References Cited

U.S. PATENT DOCUMENTS

2004/0092583 A1* 5/2004 Shanahan-Prendergast . 514/469
2006/0193789 A1* 8/2006 Tamarkin et al. ............... 424/47

OTHER PUBLICATIONS

Domingo E. Galliano, Jr., MD, Charlotte County Edition/Spring, 2008/Florida Health Care News/ p. 11.*
The Merck Manual, 17th edition, pp. 326-327 (1999).*
Sidky Y. A. et al.: "Inhibition of Murine Tumor Growth by an Interferon-Inducing Imidazoquinolinamine" Cancer Research, vol. 52, No. 13, 1992, pp. 3528-3533.
Fleshner Phillip et al.: "Practice Paramaters for Anal Squamous Neoplasms" Nov. 21, 2007, Diseases of the Colon & Rectum, Springer-Verlag, NE, pp. 2-9.
Lipka E. et al.: "Evaluation of imiquimod and analogues with respect to their oral delivery potential" Proceedings of the Int'l. Symp. Control. Rel. Bioact. Mater., 1997 US, No. 24, 1997, pp. 337-338.
Carrasco Daniel et al.: "Treatment of anogenital warts with imiquimod 5% cream followed by surgical excision of residual lesions." Journal of the American Academy of Dermatology, vol. 47, No. 4 Suppl, Oct. 2002, pp. 5212-5216.
Diakomanolis Emmanuel et al.: "Treatment of high-grade vaginal intraepithelial neoplasia with imiquimod cream." The New England Journal of Medicine, Aug. 1, 2002, vol. 347, No. 5, p. 374.
Pfenninger John L. et al.: "Common anorectal conditions" Obstetrics and Gynecology, vol. 98, No. 6, Dec. 2001, pp. 1130-1139.
International Search Report dated Apr. 1, 2009, issued in related International Application No. PCT/EP2008/011088.
Burmer, G. C. et al., "Neoplastic Progression Ulcerative Colitis: Histology, DNA Content, and Loss of a p53 Allele", *Gastroeterology*, vol. 103(5), p. 1602-10, Nov 1992.
Hussain, S.P. et al, "Increased p53 Mutation Load in Noncancerous Colon Tissue from Ulcerative Colitis: A Cancer-Prone Chronic Inflammatory Disease", *Cancer Research*, vol. 60, p. 3333-3337, Jul. 1, 2000.
Van Den Berg, F.M. et al., "Expression of the Nuclear Oncogene p53 in Colon Tumours", *Journal of Pathology*, vol. 157, p. 193-199, 1989.

* cited by examiner

*Primary Examiner* — Phyllis G. Spivack
(74) *Attorney, Agent, or Firm* — Venable LLP; Keith G. Haddaway

(57) ABSTRACT

The invention relates to treating colorectal polyps and pre-cancercerous colorectal changes by topical administration of immunomodulating drugs of the imidazoquinoline family, such as imiquimod (1-(2-methylpropyl)-1H-imidazo[4,5-c]quinolin-4-amine), resiquimod (4-amino-α,α-dimethyl-2-ethoxymethyl-1H-imidazo[4,5-c]quinoline-1-ethanol), sotirimod (2-methyl-1-(2-methylpropyl)-1H-imidazo[4,5-c][1,5]naphthyridin-4-amine).

15 Claims, 1 Drawing Sheet

TREATMENT OF COLORECTAL POLYPS WITH IMIDAZOQUINOLINE DERIVATIVES

The present invention relates to treating of colorectal diseases such as polypes, precancerous stages, and prevention and adjuvant treatment of colorectal cancer by topical administering immunomodulating drugs of the imidazoquinoline family such as imiquimod (1-(2-methylpropyl)-1H-imidazo[4,5-c]quinolin-4-amine), resiquimod (4-amino-α,α-dimethyl-2-ethoxymethyl-1H-imidazo[4,5-c]quinoline-1-ethanol), sotirimod (2-methyl-1-(2-methylpropyl)-1H-imidazo[4,5-c][1,5]naphthyridin-4-amine). Surprisingly, these immunomodulating imidazoquinoline derivatives inhibit the transformation of precancerous gastrointestinal cells into malignant colorectal tumour cells.

The use of different imidazoquinoline derivatives may result in a more effective and safer treatment of the above mentioned colorectal diseases.

Colorectal polyps are fairly common in middle-aged and older adults and often do not have noticeable symptoms. About 50% of the people over the age of 60 have polyps in the colon. Their potential to become cancerous makes it important that they are taken seriously. While the vast majority of polyps are benign (noncancerous), nearly all colon cancers evolve from benign polyps. Carcinomas account for more than 80% of human cancers, with skin, lung, colon, breast, prostate, and uterus being the most frequent sites.

Colon polyps vary greatly in size, shape and number. The two main types are hyperplastic and adenomatous. Hyperplastic polyps are the most common and typically do not become cancerous. Adenomatous polyps are more likely to become cancerous.

In general, tumour development follows three distinct phases: initiation, promotion, and progression. Cancer prevention approaches inter alia include enhancing host defence mechanisms against cancer, chemoprevention, and others. In spite of improvements in early detection and treatment of cancer, overall mortality rates have not declined in the last 30 years.

There are several possibilities to lower the risk of the cancerous development of a polyp. One possibility to prevent colon polyps from developing to cancer represents diets low in fat and high in fibre. Certain vitamins also protect against colon cancer, namely vitamins C and E. Non-steroidal anti-inflammatory medications, such as aspirin reduce the formation of polyps, although non-steroidal anti-inflammatory medications are not advocated as a means to prevent colon polyps.

Of the three phases of tumor development, the promotion phase consists of the expansion of mutated cells to form an actively proliferating, multicellular premalignant lesion. This promotion phase of carcinogenesis may provide the best targets for cancer prevention. A novel and special form of cancer prevention is the so-called chemoprevention. Chemoprevention, by definition, is the use of agents to slow the progression of, reverse, or inhibit carcinogenesis, thereby lowering the risk of developing invasive or clinically significant disease.

If a tumour is established, several types of standard treatment can be used. These include surgery, chemotherapy, radiation therapy, and biologic therapy. The biologic therapy is a treatment that uses the patient's immune system to fight cancer. Body-own substances or drugs are used to boost or restore the body's natural defences against cancer. This type of cancer treatment is also called biotherapy or immunotherapy.

Imidazoquinolines: Imiquimod is an immunomodulatory compound in the imidazoquinoline family that displays both antiviral and antitumor effects (Diebold SSet al. Innate antiviral responses by means of toll-like receptor (TLR)-7-mediated recognition of single-stranded RNA. Science 204; 303: 1529-1531; Barnetson RSet al . Imiquimod induced regression of clinically diagnosed superficial basal cell carcinoma is associated with early infiltration by CD4 T cells and dendritic cells Clin. Exp. Dermatol 2004; 29: 639-643). Imiquimod was shown to exert its effects mainly through TLR-7 (Hemmi H et al. Small anti-viral compounds activate immune cells via the TLR 7 MyD88-dependent signaling pathway. Nat. Immunol 2002; 3:196-200). Imiquimod effectively inhibits the progression of actinic keratosis (AK) into invasive skin cancer, usually squamous cell carcinoma (SCC). Although imiquimod does not exert any direct antineoplastic activities (Schön M et al. Tumor-selective induction of apoptosis and the small-molecule immune response modifier imiquimod. J Natl. Cancer Inst. 2003, 95:1138-49), it has shown good efficacy against a variety of skin tumors and of other origin. In mice, oral treatment with imiquimod significantly inhibited the development of MC-26 colon carcinoma. The anti-tumor effects of imiquimod were significantly abrogated by an antiserum to murine interferon (IFN)-α, suggesting that the antitumor effect was to a substantial extent mediated by IFN induction (Sidky Y A et al. Inhibition of murine tumor growth by an interferon-inducing imidazoquinolinamine. Cancer Res 1992; 52:3528-33).

The exact mode of action of imiquimod and related compounds against cancerous cells is complex and still unknown.

There is evidence that imiquimod is able to promote apoptosis of different malign skin cells (Inglefield J R, et al. Apoptotic responses in squamous carcinoma and epithelial cells to small-molecule toll-like receptor agonists evaluated with automated cytometry. J Biomol Screen 2006; 11:575-85).

Immunotherapy: Cell-mediated immune responses are an essential aspect of tumour-host interactions in colorectal cancers. The progression from precancerous (adenomatous) colon polyps to malignant colorectal cancer depends on a complex pathway involving the activities of activated T lymphocytes. The immune response is initiated when either cytotoxic T lymphocyte CD8+ cells or CD4+ T-helper cells recognize the antigen from a human cancer cell. The cell-mediated response is largely initiated and controlled by the actions of various cytokines, which exert profound effects on T-cell proliferation, cell-cell adhesion, apoptosis, and host immunity. The existence of an immune response to colon cancer is supported by studies of immunological treatments in humans and transplantable murine cancer models in animals. IL-2, IL-12, IFN-γ, TNF-α, and TNF-related apoptosis-inducing ligand (TRAIL) are implicated in enhancing cytotoxic and apoptotic effects in response to colon adenomas. In addition, growth factors, cytokines and immunosuppressive factors may play a crucial role in the growth and survival of premaligant colorectal tissue.

Imiquimod has proven to be effective in the treatment of actinic keratosis (AK) also a precancerous stage. Imiquimod effectively clears AK lesions and prevents progression to SCC and other malignant skin tumours.

The topical application of imidazoquinolines to other cell types, especially to gastrointestinal epithelial cells, is a new approach. Surprisingly, immunomodulating drugs as imiquimod, resiquimod and sotirimod also inhibited the apoptosis not only of epidermal cells (e.g. keratinocytes) but also of gastrointestinal epithelial cells indicating that it is capable of inhibiting the cancerous development of the colon polyp.

EXPERIMENTAL PART

Figure 1:
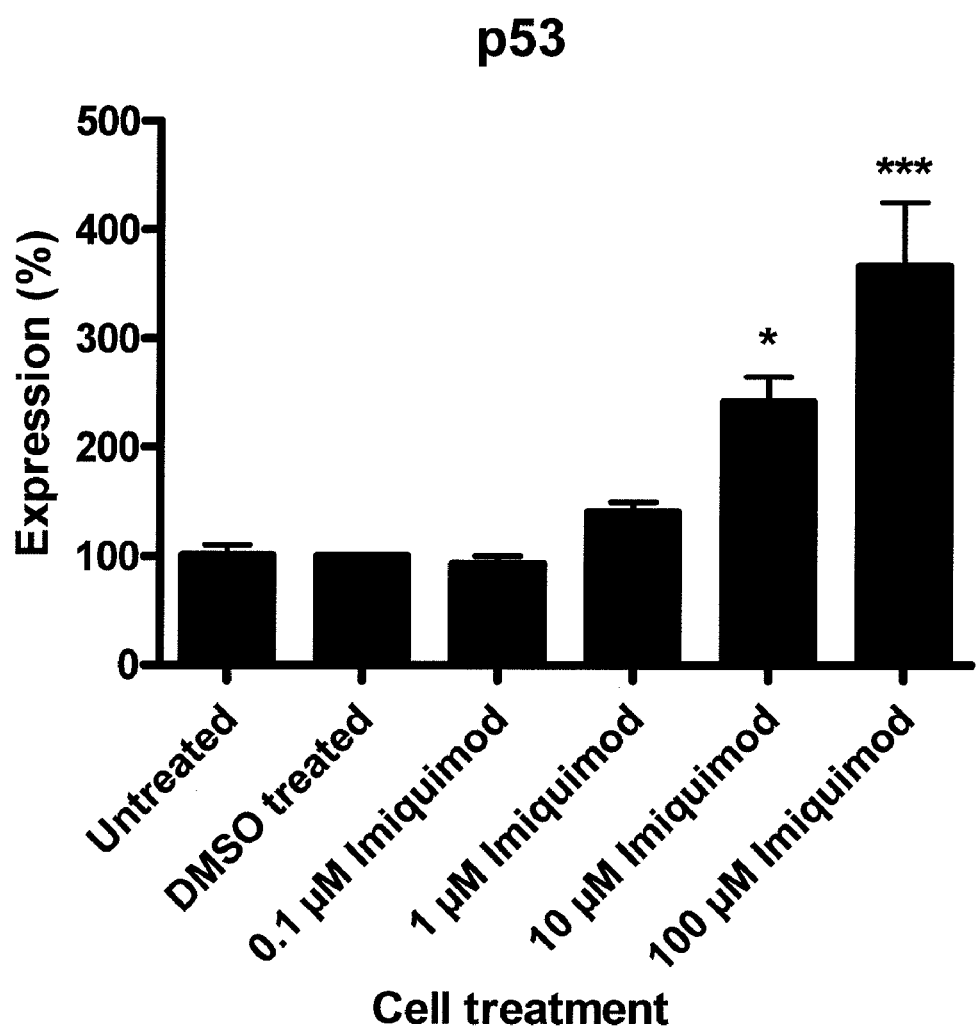
FIG. 1 shows the dose dependent effect of imiquimod on the expression of p53 in Caco-2 cells was assessed by quantitative real-time RT-PCR.

The influence of imiquimod on apoptotic changes was investigated by using colon epithelial cells. The Caco-2 cell line is widely used in in vitro assays to predict the absorption rate of candidate drug compounds across the intestinal epithelial cell barrier. Therefore this cell line was used to investigate the effects of imiquimod on p53 expression. p53 is a transcription factor that regulates the cell cycle and hence functions as a tumor suppressor. This tumor suppressor gene is a very important element in the multiple step progression from benign hyper proliferation to the malignant disease.

The p53 tumour suppressor appears to be essential to prevent growth and survival of damaged and abnormal cells. The p53 protein is a tumour suppressor encoded by a gene whose disruption is associated with approximately 50 to 55 percent of human cancers. The p53 protein acts as a checkpoint in the cell cycle, either preventing or initiating programmed cell death. In other words, p53 is a built-in tumour suppressor. The p53 molecule can be inactivated in several ways: i) In certain families, p53 mutations are inherited; ii) DNA tumour viruses, such as the human adenovirus and papilloma virus, can bind to and inactivate the p53 protein function, altering cells and initiating tumour growth. There are differences in p53 expression in various tissues. Similarly, that p53 gene regulation is different in human monocytes and lymphocytes. Consequently, changes in the skin are different from changes observed in other tissues.

Methods

Imiquimod was dissolved in dimethyl sulfoxide (DMSO). Stock concentration was 10 mg/ml. From these stocks stepwise dilutions were prepared. The final concentrations used for all compounds ranged from 0.1 μg/ml up to 100 μg/ml. The final concentration of DMSO was 0.1%.

The colorectal adenocarcinoma cell line Caco-2 was obtained from ATCC [American Type Culture Collection], Wesel, Germany. The cells were plated in 24-well plates (BD Bioscience, Heidelberg, Germany). The cells were cultured in DMEM supplemented with 10% heat-inactivated foetal bovine serum and 10% non essential amino acids in a humidified atmosphere containing 5% $CO_2$ at 37° C. When confluent, the cells were washed and resuspended in serum-free Dulbecco's Modified Eagle Medium (DMEM) at $10^6$ cells $ml^{-1}$. Cells ($1 \times 10^6$ cells/ml) were incubated with different concentrations of test substances.

RNA was prepared from frozen lysates using RNeasy, Qiagen (Hilden, Germany). One-tube Reverse Transcriptase-Polymerase Chain Reaction (RT-PCR) was performed using Quantitect Probe RT-PCR Kit from QIAGEN (Hilden, Germany). Expression of p53 was determined in relation to beta-actin by real time RT-PCR using SYBR Green assays on an ABI Prism 7900. Assays were purchased from QIAGEN, Hilden, Germany (p53: QT00060235). Quantity of mRNA was calculated using AACT method. For each RT-PCR the threshold cycle (CT) was determined, being defined as the cycle at which the fluorescence exceeds 10 times the standard deviation of the mean baseline emission for cycles 3 to 10. β-actin was used as a housekeeping gene to normalize mRNA levels: $C_t$ (Parameter)–$C_t$ (β-actin)=$\Delta C_t$ (Parameter). This value was set in relation to the vehicle control which represents mRNA levels of untreated stimulated cells: $\Delta C_t$ (Parameter stimulated)–$\Delta C_t$ (Parameter vehicle)=$\Delta\Delta C_t$ (Parameter).

The relative mRNA level for compound X was then calculated as $2^{-\Delta\Delta ct} * 100\%$ based on the results of control experiments with an efficiency of the PCR reaction of approximately 100% (according PE Applied Biosystems User Bulletin #2; ABI PRISM 7700 Sequence Detection System, 1997).

Statistical analysis was performed using GraphPad Prism Version 5 and one-way ANOVA test followed by Dunnett's post-hoc analysis.

The dose dependent effect of imiquimod on the expression of p53 in Caco-2 cells was assessed by quantitative real-time RT-PCR (FIG. 1).

Imiquimod in concentrations up to 100 μM increases p53 mRNA expression dose dependently. At concentrations of 10 and 100 μM imiquimod the increase in p53 mRNA levels reached statistical significance.

Compared to $p16^{INK4a}$, p53 is not influenced uniformly by imiquimod. In patients with Actinic Keratoses, no differences in gene expression for p53 were found under imiquimod therapy Consequently, it could not be expected that imidazoquinoline derivatives such as imiquimod can increase the expression of the tumour suppressor p53 in cells of the gastrointestinal tract indicating their beneficial effect in the treatment of precancerous/cancerous states.

These findings indicate, that imiquimod has a beneficial influence on the expression level of the tumour suppressor gene in gastrointestinal cells. This effect of imiquimod is probably crucial for the treatment of colorectal polyposis/colon polyps, prevention of colorectal carcinoma and adjuvant treatment of colorectal cancer together with conventional therapy like surgery.

EXAMPLES

The therapy contemplated by this invention comprises administering imiquimod or other imidazoquinoline derivates such as resiquimod, sotirimod to treat the existing pathological condition, the colon polyps/polyposis with the aim to reduce the probability of a cancerous transformation, to slow down the progression of the disease.

The compounds may be administered topically (rectally or directly on the tissue during surgery), in form of a solution, cream, enema or foam. The compounds may be used prophylactically or after the onset of symptoms has occurred or adjuvant to conventional therapy like surgery or adjuvant to colorectal polyp removal during coloscopy.

Preparations containing the active drug are to be applied 1-7 times, preferably 1-5 times per week for several weeks.

The preferred dose is 1 mg to 1000 mg imiquimod, more preferably 10 to 100 mg 3 times per week for 16 weeks.

The total amount of imiquimod can be at least 0.1 percent by weight, and no more than 9 percent by weight. In certain embodiments, the total amount of imiquimod can be at least 0.5 percent by weight, and no more than 9 percent by weight, based on the total weight of the composition (unless otherwise indicated, all percentages provided herein are weight/weight with respect to the total weight of the composition), although in some embodiments the composition may contain an amount of imiquimod outside of this range. For example, the composition may include imiquimod at a concentration of 0.1%, 0.5% 1%, 2%, 3%, 4%, 5%, 6%, 7%, 8% or 9%.

The total amount of sotirimod or resiquimod can be at least 0.001 percent by weight, and no more than 9 percent by weight. In certain embodiments, the total amount of sotirimod or resiquimod can be at least 0.1 percent by weight, and no more than 9 percent by weight, preferably at least 0.5 percent by weight, and no more than 9 percent by weight, based on the total weight of the composition (unless otherwise indicated, all percentages provided herein are weight/weight with respect to the total weight of the composition), although in some embodiments the composition may contain an amount of sotirimod or resiquimod outside of this range. For example, the composition may include sotirimod or resiquimod at a concentration of 0.001%, 0.01%, 0.1%, 0.5% 1%, 2%, 3%, 4%, 5%, 6%, 7%, 8% or 9%.

The invention claimed is:

1. A method of treatment of colorectal polyps/polyposis by application of an imidazoquinoline derivative selected from the group consisting of imiquimod, resiquimod and sotirimod.

2. The method of treatment according to claim 1, wherein the patient is a HIV or immunocompromised patient.

3. The method according to claim 1, wherein the imidazoquinoline derivative is administered topically, in form of a solution, cream or foam.

4. The method according to claim 1, wherein the imidazoquinoline derivative is administered 1-7 times per week for several weeks.

5. The method according to claim 4, wherein the imidazoquinoline derivative is administered 1-5 times per week for several weeks.

6. A method of treatment of precancerous colorectal changes by application of an imidazoquinoline derivative selected from the group consisting of imiquimod, resiquimod and sotirimod.

7. The method according to claim 6, wherein the imidazoquinoline derivative is administered 1-7 times per week for several weeks.

8. The method according to claim 7, wherein the imidazoquinoline derivative is administered 1-5 times per week for several weeks.

9. The method of treatment according to claim 6, wherein the patient is a HIV or immunocompromised patient.

10. The method according to claim 6, wherein the imidazoquinoline derivative is administered topically, in form of a solution, cream or foam.

11. A method of adjuvant treatment of colorectal polyps/polyposis by application of an imidazoquinoline derivative selected from the group consisting of imiquimod, resiquimod and sotirimod.

12. The method according to claim 11, wherein the imidazoquinoline derivative is administered 1-7 times per week for several weeks.

13. The method according to claim 12, wherein the imidazoquinoline derivative is administered 1-5 times per week for several weeks.

14. The method of treatment according to claim 11, wherein the patient is a HIV or immunocompromised patient.

15. The method according to claim 11, wherein the imidazoquinoline derivative is administered topically, in form of a solution, cream or foam.

* * * * *